United States Patent [19]

Dean et al.

[11] Patent Number: 5,976,496
[45] Date of Patent: *Nov. 2, 1999

[54] LABELED SOMATOSTATIN ANALOGS FOR IMAGING CARDIOVASCULAR DISEASE

[75] Inventors: Richard T. Dean; John Lister-James, both of Bedford, N.H.

[73] Assignee: Diatide, Inc., Londonderry, N.H.

[ * ] Notice: This patent is subject to a terminal disclaimer.

[21] Appl. No.: 08/976,995

[22] Filed: Nov. 24, 1997

Related U.S. Application Data

[63] Continuation-in-part of application No. 08/253,973, Jun. 3, 1994.

[51] Int. Cl.⁶ .......................... A61K 51/00; A61M 36/14
[52] U.S. Cl. .................. 424/1.69; 424/1.11; 424/1.65; 424/9.1; 530/311; 530/317; 530/300; 534/14
[58] Field of Search ....................... 424/1.11, 1.65, 424/1.69, 9.1, 9.3, 9.4, 9.5, 9.6; 530/300, 311, 317, 324–330; 534/7, 10–16; 206/223, 569–570

[56] References Cited

U.S. PATENT DOCUMENTS

| | | | |
|---|---|---|---|
| 5,409,894 | 4/1995 | Handley | 514/8 |
| 5,506,339 | 4/1996 | Coy et al. | 530/311 |
| 5,556,939 | 9/1996 | Flanagan et al. | 530/311 |
| 5,569,647 | 10/1996 | Fauchere et al. | 514/11 |
| 5,783,170 | 7/1998 | Dean | 424/1.69 |
| 5,833,942 | 11/1998 | Dean et al. | 424/1.41 |
| 5,843,401 | 12/1998 | Dean et al. | 424/1.69 |

FOREIGN PATENT DOCUMENTS

| | | | |
|---|---|---|---|
| 0607103 A2 | 7/1994 | European Pat. Off. | C07K 7/26 |
| WO 95/33497 | 12/1995 | WIPO . | |
| WO96/37239 | 11/1996 | WIPO | A61K 51/00 |
| WO97/01579 | 1/1997 | WIPO | C07K 14/655 |
| WO97/11962 | 4/1997 | WIPO | C07K 7/00 |

OTHER PUBLICATIONS

Diatide Prospectus excerpt of Jun. 13, 1996, pp. 1, 31, 36–37.
M.L. Foegh, "Accelerated Cardiac Transplant Atherosclerosis/Chronic Rejection in Rabbits: Inhibition by Angiopeptin" *Transplantation Proceedings* 25(2):2095–2097 (1993).
B.M. Meiser et al., "Prevention and Treatment of Graft Vessel Disease After Heart Transplantation" *Transplantation Proceedings* 27 (3) 1931–1935 (1995).
Th. Wahlers et al., "Coronary Vasculopathy Following Cardiac Transplantation and Cyclosporine Immunosuppression: Preventive Treatment with Angiopeptin, A Somatostatin Analog" *Transplantation Proceedings* 26 (5):2741–2742 (1994).

*Primary Examiner*—S. Mark Clardy
*Assistant Examiner*—Dameron Jones
*Attorney, Agent, or Firm*—Patricia A. McDaniels

[57] ABSTRACT

The present invention provides methods and kits for detecting cardiovascular disease in a living mammal, using a labeled form of a somatostatin analog. The methods and kits of the invention provide early detection of atherosclerotic plaque, in particular, unstable atherosclerotic plaque, thus allowing therapeutic intervention prior to acute and potentially fatal incidents of cardiovascular disease.

26 Claims, No Drawings

LABELED SOMATOSTATIN ANALOGS FOR IMAGING CARDIOVASCULAR DISEASE

This application is a continuation-in-part of U.S. patent application Ser. No. 08/253,973, filed Jun. 3, 1994.

The present invention relates to the field of medical imaging. More specifically, the invention relates to improved methods of diagnostic imaging of cardiovascular disease, in particular at early stages of development of such disease, using labeled analogs of the inhibitory peptide somatostatin.

BACKGROUND OF THE INVENTION

Cardiovascular disease is a major health problem throughout the world, having a particularly high incidence in the United States, where during each year approximately 1,500,000 persons suffer a heart attack, approximately 400,000 to 500,000 persons suffer a stroke, and approximately 5,600,000 persons suffer angina. In the United States, heart attack (i.e., myocardial infarction) is in fact the leading cause of death, and stroke is the third leading cause of death. Unstable angina, i.e., severe constricting pain of coronary origin that occurs in response to less exercise than usually required to induce angina, may be associated with sudden cardiac death. A great need exists for early, accurate diagnosis of cardiovascular diseases.

Heart attack, angina, and stroke are caused by stenosis, or narrowing, of arteries, which is closely related to formation of atherosclerotic plaque, or atherogenesis. Until recently, cardiovascular lesions were believed to form gradually, and acute clinical episodes were believed to occur only when the stenosis exceeds 40% of the cross-sectional area of the original blood vessel's lumen. However, improved therapeutic methods such as thrombolytic therapy during acute myocardial infarction have revealed that atherosclerotic lesions most likely to precipitate a heart attack often were not associated with a high degree of stenosis. From autopsy studies, a class of atherosclerotic plaque has been identified, termed unstable or vulnerable plaque, which is associated with acute myocardial infarction and which is particularly susceptible to rupture. A large proportion of cardiovascular disease is now believed to progress through one or more subclinical episodes in which unstable plaque is disrupted with local thrombin activation and subsequent healing. Acute myocardial infarction is now believed to result from formation of an occluding thrombus, or blood clot, at the site of a ruptured atherosclerotic plaque. Unstable angina is also believed to be associated with thrombus formation, while other forms of angina are believed to be associated with stenoses that are not associated with thrombosis. The presence of severe stenoses is now considered to be a marker for less occlusive, unstable plaque that may be prone to rupture. No means for identifying unstable plaque prior to an acute event or death now exists, since current angiographic methods can only detect plaque when the extent of occlusion approaches 50% of the blood vessel luminal cross-section.

Atherogenesis is believed to begin with an initial lesion that appears as a fatty streak on the inner surface of an artery, consisting of two to five layers of lipid filled macrophages known as foam cells. Subsequently an intermediate fibro-fatty lesion forms, consisting of twenty to thirty alternating layers of foam cells together with T lymphocytes and smooth muscle cells that separate the layers. Ultimately a fibrous plaque forms, in which a fibrous cap covers a central necrotic zone that may contain lipid, cells, and necrotic debris. A region containing numerous smooth muscle cells may also lay beneath the central necrotic lesion. The fibrous cap of an atherosclerotic plaque consists of layers of smooth muscle cells surrounded by a dense connective tissue matrix containing basement membrane, collagen fibers, and proteoglycan dispersed throughout the matrix. Some fibrous caps are inherently weaker than others, and these weak fibrous caps are rupture-prone.

Currently available methods for diagnosing cardiovascular disease employ a variety of imaging technologies, including conventional x-ray imaging, computerized tomography, magnetic resonance imaging, ultrasound, and nuclear medicine imaging. Contrast agents and radiopharmaceuticals capable of accumulating at the site of a lesion are commercially available for use in imaging cardiovascular disease, for example in angiography and venography. However, angiograms do not detect or measure the degree of atherosclerosis accurately, since they do not detect plaques that cause no stenosis. A variety of radiopharmaceuticals have been used to study or detect cardiovascular disease, such as the nuclides $^{201}$Tl, $^{99m}$Tc, $^{133}$Xe; or the nuclide labeled metabolic agents $^{11}$C-2-deoxy-D-glucose, $^{18}$F-2-fluorodeoxy-D-glucose, [1-$^{11}$C]- and [$^{123}$I]-β-methyl fatty acid analogs, $^{13}$N-ammonia; or infarct avid agents such as $^{99m}$Tc-tetracycline, $^{99m}$Tc-pyrophosphate, $^{203}$Hg-mercurials, $^{67}$Ga citrate, and the like. Improved imaging agents for diagnosis of cardiovascular lesions, especially for pre-acute event diagnosis of unstable atherosclerotic plaque, are needed.

Somatostatin is a tetradecapeptide that inhibits release of insulin and glucagon from the pancreas, inhibits growth hormone release from the hypothalamus, and reduces gastric secretions. A large number of somatostatin analogs have been developed for treatment of diseases such as diabetes, acromegaly, ulcers, pancreatitis and neuroendocrine tumors. Foegh (1993) *Transplantation Proceedings* 25, 2095–2097; Akyurek, et al. (1993) *Transpl. Int.* 8, 103–110;, disclose that angiopeptin, an analog of somatostatin, inhibits proliferation of smooth muscle cells at the site of induced lesions in blood vessels of animals. Wahlers, et al. (1994) *Transplantation Proceedings* 26, 2741–2742; and Meiser, et al. (1995) *Transplantation Proceedings* 27, 1931–1935 disclose clinical studies in which angiopeptin was used to treat post heart transplantation cardiovascular lesions in humans. U.S. Pat. No. 5,506,339 discloses that specific somatostatin analogs may be used to treat atherosclerosis associated with vascular grafts and restenosis following angioplasty, and U.S. Pat. No. 5,569,647 discloses that specific somatostatin analogs may be used to inhibit proliferation of vascular smooth muscle cells. The therapeutic efficacy of the somatostatin analogs of U.S. Pat. Nos. 5,506,339 and 5,569,647 is not predictive that such analogs act by accumulating at the site of atherosclerotic plaque. Many drugs are therapeutically effective yet do not specificaly localize at the anatomical site which is affected.

Somatostatin analogs have also been developed as imaging agents, in particular, as components of agents for imaging tumors. EP 607103 discloses specific radio-labeled somatostatin analogs for use as imaging agents to visualize somatostatin receptor accumulation, in particular, in somatostatin receptor positive tumors and metastases, in inflammatory or autoimmune disorders exhibiting somatostatin receptors, in tuberculosis, or in organ rejection after transplantation. WO 97/01579 discloses use of somatostatin analogs for imaging somatostatin receptor positive tissues and cells, in particular, tumors, metastases, inflammatory disorders and autoimmune disorders. Neither of these references suggests that somatostatin analogs may be employed to image atherosclerotic plaque.

SUMMARY OF THE INVENTION

The present inventors have discovered that detectably labeled somatostatin analogs may be employed to image cardiovascular lesions. In particular, such labeled somatostatin analogs may be used to image unstable atherosclerotic plaque and thus to resolve a previously unmet need. By virtue of the present invention, the incidence of acute cardiovascular illness may be reduced through detection of unstable plaque in a patient and administration of appropriate treatment prior to the occurrence of a potentially debilitating or fatal myocardial infarction. Prior to the present invention, detection of unstable plaque has not been possible.

In one embodiment, the invention provides a method of imaging a lesion in a cardiovascular system of a living mammal, comprising the steps of administering to the mammal a diagnostically effective amount of a labeled somatostatin analog, exposing the mammal to an imaging apparatus capable of detecting the analog, and detecting accumulation of the analog in the cardiovascular system.

In another embodiment, the invention provides a kit for imaging a cardiovascular lesion comprising a sealed vial containing a predetermined quantity of a labeled or unlabeled form of a somatostatin analog and written instructions for accomplishing cardiovascular imaging using a labeled form of the analog.

DETAILED DESCRIPTION OF THE INVENTION

The patent and scientific literature referenced herein establish the knowledge available to those with skill in the art. The issued U.S. patents and allowed applications are hereby incorporated by reference.

The methods and kits of the present invention allow detection of lesions in the cardiovascular system of a mammal using a labeled form of a somatostatin analog. As defined herein, a cardiovascular lesion includes atherosclerotic plaque at any stage of atherogenesis, e.g., initial fatty streaks, intermediate fibrofatty lesions, and fibrous plaque are all considered to be cardiovascular lesions which are detectable by the methods and kits of the present invention. Any cardiovascular lesion may be detected using a labeled form of a somatostatin analog in accordance with the present invention. Preferably, highly stenotic plaque, i.e., plaque that occludes more than about 40% of the blood vessel luminal cross-section, is detectable using the methods and kits of the invention. More preferably, non-critically stenotic plaque, i.e., plaque that occludes less than about 40% of the blood vessel luminal cross-section, is detectable using the methods and kits of the invention. Most preferably, unstable atherosclerotic plaque is detectable using the methods and kits of the invention.

As defined herein, a somatostatin analog includes peptides or peptidomimetic compounds which bind to somatostatin receptors in an in vitro somatostatin receptor binding assay such as the assay disclosed in WO 95/31221. Any somatostatin analog may be employed to detect cardiovascular lesions in accordance with the methods and kits of the invention. For example, peptide somatostatin analogs such as those described in allowed U.S. Pat. application Ser. No. 07/902,935, U.S. Pat. No. 5,620,675, U.S. Pat. No. 4,650,787, U.S. Pat. No. 5,556,939, U.S. Pat. No. 5,569,647, U.S. Pat. No. 5,506,339, WO 94/00489, WO 97/11962, WO 97/01579, WO 96/37239, WO 90/06949, EP 607103, EP 515313, GB 2241167, and the like may be used in the methods and kits of the invention. Both cyclic and linear peptide somatostatin analogs may be used in the methods and kits of the invention. Peptidomimetic somatostatin analogs prepared, for example, according to the principles set forth in U.S. Pat. No. 5,550,251, U.S. Pat. No. 5,250,564, WO 97/28172, WO 95/11686, WO 93/17032, WO 93/12084, WO 93/11731, and the like, may also be used in the methods and kits of the invention. Preferably, the somatostatin analogs of U.S. Pat. No. 5,620,675 are employed in the methods and kits of the invention. More preferably, the somatostatin analogs of U.S. Pat. No. 5,569,647 and U.S. Pat. No. 5,506,339 are employed in the methods and kits of the invention. Most preferably, the somatostatin analogs of allowed U.S. Pat. application Ser. No. 07/902,935 and WO 94/00489 are employed in the methods and kits of the invention. Specific embodiments of preferred peptide somatostatin analogs have the structures set forth below:

cyclo.(N—CH$_3$)F.YW$_D$KV.Hcy(CH$_2$CO.($\delta$-Orm)GCK.amide)

cyclo.(N—CH$_3$)F.YW$_D$KV.Hcy(CH$_2$CO.($\beta$-Dap)KCK.amide)

cyclo.(N—CH$_3$)F.YW$_D$KV.Hcy(CH$_2$CO.CGC.amide)

cyclo.(N—CH$_3$)F.YW$_D$KV.Hcy(CH$_2$CO.CGC)

cyclo.(N—CH$_3$)F.YW$_D$KV.Hcy(CH$_2$CO.($\epsilon$-K)GC.amide)

cyclo.(N—CH$_3$)F.YW$_D$KV.Hcy(CH$_2$CO.GGC.amide)

cyclo(N—CH$_3$)FFW$_D$KTFCC$_{Acm}$GC$_{Acm}$.amide)

cyclo(N—CH$_3$)FYW$_D$KV.Hcy(CH$_2$COGGCK. amide)

cyclo(N—CH$_3$)FYW$_D$KV.Hcy(CH$_2$CO($\epsilon$-K)GCK.amide)

cyclo(N—CH$_3$)FYW$_D$KV.Hcy(CH$_2$COGGCR.amide)

cyclo(N—CH$_3$)FYW$_D$KV.Hcy(CH$_2$CO($\epsilon$-K)KC.amide)

cyclo(N—CH$_3$)FYW$_D$KV.HcyCH$_2$COGGC.Orn.amide)

cyclo(N—CH$_3$)FYW$_D$KV.Hcy(CH$_2$CO($\beta$-Dap)KC.amide)

cyclo.(N—CH$_3$)FYW$_D$KV.Hcy(CH$_2$CO.KKKKK($\epsilon$-K)GC.amide)

cyclo.(N—CH$_3$)F.YW$_D$KV.Hcy(CH$_2$CO.GGCKK.amide)

cyclo.(N—CH$_3$)F.YW$_D$KV.Hcy(CH$_2$CO.K($\epsilon$-K)GC.amide)

cyclo.(N—CH$_3$)F.YW$_D$KV.Hcy(CH$_2$CO.C$_{Acm}$GC$_{Acm}$.amide)

cyclo.(N—CH$_3$)F.YW$_D$KV.Hcy(CH$_2$CO.CGCE.amide)

As used herein, the following amino acids and amino acid analogues are intended to be represented by the following abbreviations: Ac is an acetyl group; ma is a mercaptoacetic acid group; Aca is 6-aminocaproic acid; Hcy is homocysteine; Hhc is homohomocysteine (3-mercaptopropylglycine); Pen is penicillamine; Mob is the sulfhydryl protecting group 4-methoxybenzyl; Acm is the sulfhydryl protecting group acetamidomethyl; Aib is aminoisobutyric acid; Nal is 2-naphthylalanine; Ain is 2-aminoindan-2-carboxylic acid; Hly is homolysine; Achxa is 4-amino-cyclohexylalanine; Amf is 4-aminomethyl-phenylalanine; Aec is S-(2-aminoethyl)cysteine; Apc is S-(3-aminopropyl)cysteine; Aes is O-(2-aminoethyl)serine; Aps is O-(3-aminopropyl)serine; Abu is 2-aminobutyric acid; Nva is norvaline; F$_D$ is D-phenylalanine; W$_D$ is D-tryptophan; Y$_D$ is D-tyrosine; Cpa is L-(4-chlorophenyl)alanine; Thp is 4-amino-tetrahydrothiopyran-4-carboxylic acid; D-Nal is D-2-naphthylalanine; Dpg is dipropylglycine; Dap is diaminopropionic acid; and Nle is norleucine. All naturally-occurring amino acids are abbreviated using standard abbreviations (which can be found in G. Zubay, *Biochemistry* (2d. ed.), 1988 (MacMillen Publishing: New York) p.33.

Methods for making the peptide somatostatin analogs used in the methods and kits of the invention are known. For example, methods for making peptide somatostatin analogs such as those listed above are disclosed in allowed U.S. Pat. application Ser. No. 07/902,935. Linear peptide somatostatin analogs may be made as disclosed in U.S. Pat. No. 5,620,675. Methods for making other peptide somatostatin analogs suitable for use in the present invention are disclosed, for example, in U.S. Pat. No. 4,650,787; U.S. Pat. No. 5,556,939; U.S. Pat. No. 5,569,647; U.S. Pat. No. 5,506,339; WO 94/00489; WO 97/11962; WO 97/01579; WO 96/37239; WO 90/06949; EP 607103; EP 515313; GB 2241167, and the like. Methods for making peptidomimetic somatostatin analogs are set forth, for example, in U.S. Pat. No. 5,550,251, U.S. Pat. No. 5,250,564, WO 97/28172, WO 95/11686, WO 93/17032, WO 93/12084, WO 93/11731.

Any labeled form of a somatostatin analog may be used to detect cardiovascular lesions in accordance with the present invention. Suitable labels include radioactive labels, fluorescent labels, paramagnetic labels, heavy elements or rare earth ions suitable for use in computerized tomography, and the like. Radioactive labels are preferred. More preferably, γ-emitting radionuclides such as $^{123}$I, $^{67}$Ga, $^{111}$In, and $^{99m}$Tc, are used in the methods of the invention. Most preferably, $^{99m}$Tc is used in the methods of the invention. A label may be linked to a somatostatin analog for use in the method of the invention via any suitable linkage, so long as that linkage is stable under in vivo conditions. Suitable linkages include ionic linkages, covalent linkages, van der Waals linkages, and the like. For radioactive labels, covalent linkages are preferred. The linkage between the somatostatin analog and the label may be a direct linkage or an indirect linkage, i.e., a linkage through a chelating or label binding moiety. When a radionuclide such as $^{99m}$Tc is employed as a label, binding moieties such as those disclosed in allowed U.S. Pat. No. application Ser. No. 07/902,935; WO 94/00489; U.S. Pat. No. 5,225,180; U.S. Pat. No. 5,405,597; U.S. Pat. No. 5,443,815; and U.S. Pat. No. 5,620,675 are preferred. Methods for linking a somatostatin analog to a radiolabel binding moiety are disclosed in these patents and publications.

Cardiovascular lesions are detected in accordance with the invention by administering a diagnostically effective amount of a labeled somatostatin analog to a mammal, exposing the mammal to an imaging apparatus capable of detecting the analog, and detecting accumulation of the analog in the mammal's cardiovascular system. As used herein, a diagnostically effective amount is defined as an amount sufficient to yield an acceptable image using equipment which is available for clinical use. An effective amount of the labeled somatostatin analog may be administered in more than one dose, but is preferably administered in a single dose. Effective amounts of the labeled somatostatin analog may vary according to factors such as the degree of susceptibility of the individual; the age, sex, and weight of the individual; idiosyncratic responses of the individual; and dosimetry. Effective amounts of the labeled somatostatin analog may also vary with the particular instrument employed and film- or detector-related factors. Optimization of such factors is within the level of skill in the art. When a radioactive label is employed in the method of the invention, the unit dose may range from about 0.01 mCi to about 100 mCi. The unit dose of a radioactively labeled somatostatin analog is preferably from about 1 mCi to about 20 mCi. It should be noted that the concentration of somatostatin analog in a diagnostically effective unit dose is significantly less than the concentration of such an analog necessary to provide a therapeutically effective unit dose.

In the method of the invention, the labeled somatostatin analog is preferably administered intravenously, in combination with a pharmaceutically acceptable carrier, to a living mammal. As used herein, a pharmaceutically acceptable carrier may include any and all solvents, dispersion media, antibacterial and antifungal agents, isotonic agents, and the like. The use of such media and agents for pharmaceutically active substances is well known in the art. The labeled somatostatin analog is formulated as a sterile, pyrogen-free, parenterally acceptable aqueous solution which may optionally be supplied in lyophilized form and be reconstituted by the user. The preparation of such parenterally acceptable solutions, having due regard to pH, isotonicity, stability, and the like, is within the skill in the art.

The labeled somatostatin analog may further be administered to the mammal in an appropriate diluent or adjuvant or be co-administered with enzyme inhibitors or in a carrier such as species appropriate albumin. Pharmaceutically acceptable diluents include saline such as or aqueous buffer solutions. Many such diluents are known to those of skill in the art, such as, for example, Sodium Chloride Injection and Ringer's Injection. For administration to humans, the labeled somatostatin analog may be administered in autologous serum or plasma. Supplementary active compounds may also be co-administered with the labeled somatostatin analog, in accordance with the invention.

Any imaging apparatus may be employed in the method of the invention, so long as the apparatus is capable of detecting the labeled somatostatin analog within the cardiovascular system of a mammal. Suitable apparatus include, for example, gamma cameras, conventional x-ray apparatus, computerized tomographic apparatus, single photon emission computerized tomographic apparatus, positron emission apparatus, magnetic resonance imaging apparatus, fluorescence detectors, and the like.

The kits of the invention include a sealed vial containing a predetermined quantity of a labeled or unlabeled somatostatin analog and written instructions for accomplishing imaging of cardiovascular lesions using a labeled form of the analog. When the kit contains an unlabeled somatostatin analog, instructions and reagents for accomplishing a labeling reaction are also included. A sealed vial containing a detectable label may optionally be included in the kit of the invention. When the detectable label is intended to be a radionuclide, such as $^{99m}$Tc, an appropriate amount of a reducing agent, such as a stannous ion containing agent, a dithionite ion containing agent, or a ferrous ion containing agent, may be included. An appropriate amount of a transfer ligand, such as tartrate, gluconate, or mannitol, may also be included in the kit.

The invention is further described in the example set forth below, which is intended to illustrate the invention without limiting its scope.

EXAMPLE 1

Localization and In Vivo Imaging of
Atherosclerotic Plaque using Tc-99m Labeled
Compounds of the Invention in the
Hypercholesterolemic (HC) Rabbit Model New Zealand White (NZW) rabbits of either sex and weighing 2–3 kg were divided into two groups. The control group was housed and fed commercial rabbit chow (Purina). The HC group was fed a standardized, cholesterol-rich diet (rabbit chow mixed to a 1% w/w concentration of cholesterol) from about seven weeks until about 28 weeks of age. All animals are given water ad libitum.

Radiolabeled compounds of the invention (herein exemplified by Tc-99m labeled peptides) were prepared to a specific activity of about 140–160mCi of Tc-99m per 250–400 μg of peptide and unit doses of 7–8 mCi (12.5–20.0

μg/rabbit; 6–7 μg/kg) in 0.2 mL were prepared. Rabbits were dosed with Tc-99m labeled peptide intravenously in a lateral ear vein by slow bolus infusion (approximately 0.1 mL/min).

At approximately 2.5 h post-injection, animals were sacrificed with an intravenous dose of sodium pentobarbital. Necropsy was performed during which the aorta was removed and branching vessels were dissected free from the aortic valve to the mid-abdominal region. Using a parallel hole collimator, the aorta was imaged ex corpora. Next, the aortae were opened longitudinally and stained with Sudan IV, thereby turning atherosclerotic plaque a deep red brick color. Lipid-free and uninjured aortic endothelium retained its normal, glistening white-pink appearance under these conditions.

Experiments were performed using two Tc-99m-labeled peptides of the invention, cyclo.(N—CH$_3$)F.YW$_D$KV.Hcy(CH$_2$CO.(δOrn)GCK.amide) and
cyclo.(N—CH$_3$)F.YW$_D$KV.Hcy(CH$_2$CO.GGCR.amide).

Both groups of rabbits showed rapid systemic clearance of Tc-99m-labeled peptides. The ex corpora scintigraphic images showed that each of the HC-fed NZW rabbit aortae showed a unique pattern and intensity of plaque distribution. All the HC aortae had variable amounts of radioactivity accumulation but were consistent in their display of the greatest deposition in the region of the aortic arch, with lesser degrees of accumulation in the distal and proximal segments of the aorta.

These results demonstrate that Tc-99m labeled peptides of the invention are capable of imaging atherosclerotic plaque in an animal, with high uptake. Additionally, normal aortic tissue shows minimal uptake of labeled peptides, thereby reducing the likelihood of artifactual positive scintigraphic images.

Athough a few exemplary embodiments of this invention have been described in detail above, those skilled in the art will readily appreciate that many modifications are possible in the exemplary embodiments without materially departing from the novel teachings and advantages of the invention. For example, other somatostatin analogs are useful for imaging cardiovascular lesions. Accordingly, all such modifications are intended to be included within the scope of the invention as defined in the following claims.

What is claimed is:

1. A method of imaging a lesion in a cardiovascular system of a living mammal, comprising the steps of:
   a) administering to the mammal a diagnostically effective amount of a labeled somatostatin analog;
   b) exposing the mammal to an imaging apparatus capable of detecting the analog; and
   c) detecting accumulation of the analog in the cardiovascular system.

2. The method of claim 1, wherein the analog is selected from the group consisting of a linear somatostatin analog and a cyclic somatostatin analog.

3. The method of claim 2, wherein the analog is a cyclic somatostatin analog.

4. The method of claim 3, wherein the analog is selected from the group
cycle.(N—CH$_3$)F.YW$_D$KV.Hcy(CH$_2$CO.(δ-Orn)GCK.amide);
cyclo.(N—CH$_3$)F.YW$_D$KV.Hcy(CH$_2$CO.(β-Dap)KCK.amide);
cyclo.(N—CH$_3$)F.YW$_D$KV.Hcy(CH$_2$CO.CGC;
cyclo.(N—CH$_3$)F.YW$_3$KV.Hcy(CH$_2$CO.(ε-K)GC.amide);
cyclo.(N—CH$_3$)F.YW$_D$KV.Hcy(CH$_2$CO.GGC.amide);
cyclo(N—CH$_3$)FFW$_D$KTFCC$_{Acm}$GC$_{Acm}$ amide);
cyclo(N—CH$_3$)FYW$_D$KV.Hcy(CH$_2$COGGCK.amide);
cyclo(N—CH$_3$)FYW$_D$KV.Hcy(CH$_2$CO(ε-K)GCK.amide);
cyclo(N—CH$_3$)FYW$_D$KV.Hcy(CH$_2$COGGCR.amide);
cyclo(N—CH$_3$)FYW$_D$KV.Hcy(CH$_2$CO(ε-K)KC.amide);
cyclo(N—CH$_3$)FYW$_D$KV.Hcy(CH$_2$COGGC.Orn.amide);
cyclo(N—CH$_3$)FYW$_D$KV.Hcy(CH$_2$CO(β-Dap)KC.amide);
cyclo.(N—CH$_3$)FYW$_D$KV.Hcy(CH$_2$CO.KKKKK(ε-K)GC.amide);
cyclo.(N—CH$_3$)F.YW$_D$KV.Hcy(CH$_2$CO.GGCKK.amide);
cyclo.(N—CH$_3$)F.YW$_D$KV.Hcy(CH$_2$CO.K(ε-K)GC.amide);
cyclo.(N—CH$_3$)F.YW$_D$KV.Hcy(CH$_2$CO.C$_{Acm}$GC$_{Acm}$.amide); and
cyclo.(N—CH$_3$)F.YW$_D$KV.Hcy(CH$_2$CO.CGCE.amide).

5. The method of claim 4, wherein the analog is cyclo.(N—CH$_3$)F.YW$_D$KV.Hcy(CH$_2$CO.(δ-Orn)GCK.amide).

6. The method of claim 1, wherein the analog is labeled with a radioactive label, a fluorescent label, a paramagnetic label, a detectable heavy element or a detectable rare earth ion.

7. The method of claim 6, wherein the label is a radioactive label.

8. The method of claim 7, wherein the label is selected from the group consisting of $^{123}$I, $^{67}$Ga, $^{111}$In, and $^{99m}$Tc.

9. The method of claim 8, wherein the label is $^{99m}$Tc.

10. The method of claim 9, wherein the analog is cyclo.(N—CH$_3$)F.YW$_D$KV.Hcy(CH$_2$CO.(δ-Orn)GCK.amide).

11. A kit for imaging a cardiovascular lesion comprising:
    a) a sealed vial containing a predetermined quantity of a labeled or unlabeled form of a somatostatin analog; and
    b) written instructions for accomplishing cardiovascular imaging using a labeled form of the analog.

12. The kit of claim 11, wherein the analog is selected from the group consisting of a linear somatostatin analog and a cyclic somatostatin analog.

13. The kit of claim 12, wherein the analog is a cyclic somatostatin analog.

14. The kit of claim 13, wherein the analog is selected from the group consisting of:
cyclo.(N—CH$_3$)F.YW$_D$KV.Hcy(CH$_2$CO.(δ-Orn)GCK.amide);
cyclo.(N—CH$_3$)F.YW$_D$KV.Hcy(CH$_2$CO.(δ-Dap)KCK.amide);
cyclo.(N—CH$_3$)F.YW$_D$KV.Hcy(CH$_2$CO.CGC.amide);
cyclo.(N—CH$_3$)F.YW$_D$KV.Hcy(CH$_2$CO.GGC);
cyclo.(N—CH$_3$)F.YW$_D$KV.Hcy(CH$_2$CO.(ε-K)GC.amide);
cyclo.(N—CH$_3$)F.YW$_D$KV.Hcy(CH$_2$CO.GGC.amide);
cyclo(N—CH$_3$)FFW$_D$KTFCC$_{Acm}$GC$_{Adm}$.amide);
cyclo(N—CH$_3$)FYW$_D$KV.Hcy(CH$_2$COGGCK.amide);
cyclo(N—CH$_3$)FYW$_D$KV.Hcy(CH$_2$CO(ε-K)GCK.amide);
cyclo(N—CH$_3$)FYW$_D$KV.Hcy(CH$_2$COGGCR.amide);
cyclo(N—CH$_3$)FYW$_D$KV.Hcy(CH$_2$CO(ε-K)KC.amide);
cyclo(N—CH$_3$)FYW$_D$KV.Hcy(CH$_2$COGGC.Orn.amide);
cyclo(N—CH$_3$)FYW$_D$KV.Hcy(CH$_2$CO(β-Dap)KC.amide);
cyclo(N—CH$_3$)FYW$_D$KV.Hcy(CH$_2$CO.KKKKK(ε-K)GC.amide);
cyclo.(N—CH$_3$)F.YW$_D$KV.Hcy(CH$_2$CO.GGCKK.amide);
cyclo.(N—CH$_3$)F.YW$_D$KV.Hcy(CH$_2$CO.K(ε-K)GC.amide);
cyclo.(N—CH$_3$)F.YW$_D$KV.Hcy(CH$_2$CO.C$_{Acm}$GC$_{Acm}$.amide); and cyclo.(N—CH$_3$)F.YW$_D$KV.Hcy(CH$_2$CO.CGCE.amide).

15. The kit of claim 14, wherein the analog is cyclo.(N—CH$_3$)F.YW$_D$KV.Hcy(CH$_2$CO.(δ-Orn)GCK.amide).

16. The kit of claim 11, wherein the analog is labeled with a radioactive label, a fluorescent label, a paramagnetic label, a detectable heavy element or detectable rare earth ion.

17. The kit of claim 16, wherein the label is a radioactive label.

18. The kit of claim 17, wherein the label is selected from the group consisting of $^{123}$I, $^{67}$Ga, $^{111}$In, and $^{99m}$Tc.

19. The kit of claim 18, wherein the label is $^{99m}$Tc.

20. The kit of claim 19, further comprising a reducing agent.

21. The kit of claim 20, wherein the reducing agent is selected from the group consisting of a stannous ion containing agent, a dithionite ion containing agent, and a ferrous ion containing agent.

22. The kit of claim 19, wherein the analog is cyclo.(N—CH$_3$)F.YW$_D$KV.Hcy(CH$_2$CO.(δ-Orn)GCK.amide) and the label is $^{99m}$Tc.

23. The kit of claim 11, wherein the sealed vial contains an unlabeled from of the analog.

24. The kit of claim 23, further comprising a reducing agent.

25. The kit of claim 24, wherein the reducing agent is selected from the group consisting of a stannous ion containing agent, a dithionite ion containing agent, and a ferrous ion containing agent.

26. The kit of claim 23, wherein the analog is cyclo.(N—CH$_3$)F.YW$_D$KV.Hcy(CH$_2$CO.(δ-Orn)GCK.amide).

* * * * *